United States Patent [19]

Milianowicz et al.

[11] Patent Number: 4,933,519

[45] Date of Patent: Jun. 12, 1990

[54] CONTACT STRUCTURE FOR GROUNDING SWITCH

[75] Inventors: Stanislaw A. Milianowicz, Monroeville; Nagar J. Patel, Plum Boro; Henry J. Remic, Jr., Export; Paul T. Bottegal, Lower Burrell, all of Pa.

[73] Assignee: Westinghouse Electric Corp., Pittsburgh, Pa.

[21] Appl. No.: 239,157

[22] Filed: Aug. 31, 1988

[51] Int. Cl.[5] .......... A01H 33/18

[52] U.S. Cl. .......... 200/147 R; 200/144 R; 200/255; 200/288; 200/50 AA

[58] Field of Search .......... 200/255, 288, 50 AA, 200/147 R, 144 R

[56] References Cited

U.S. PATENT DOCUMENTS

| | | | |
|---|---|---|---|
| 2,066,024 | 12/1936 | Winter | 200/255 |
| 3,118,990 | 1/1964 | Jansson | 200/255 |
| 3,382,340 | 5/1968 | Moodie et al. | 200/255 |
| 3,588,413 | 6/1971 | Stanback | 200/255 |
| 3,603,752 | 9/1971 | Frink | 200/50 AA |
| 3,603,753 | 9/1971 | Frink | 200/50 AA |
| 3,746,817 | 5/1972 | Drown et al. | 200/50 AA |
| 3,793,494 | 2/1974 | Cleaveland | 200/50 AA |
| 4,169,973 | 10/1979 | Ramos et al. | 200/288 |

FOREIGN PATENT DOCUMENTS

| | | | |
|---|---|---|---|
| 90353 | 2/1959 | Netherlands | 200/25 S |

OTHER PUBLICATIONS

Westinghouse, "VAC Clad-M Medium Voltage Metal-Clad Switchgear" Bulletin 32-255.

Westinghouse, "World-Class Medium-Voltage Switchgear with VCP-W Vacuum Circuit Breakers", Bulletin SA-11575.

Westinghouse, "VaClad-W The New Standard of World-Class Performance".

*Primary Examiner*—Robert S. Macon
*Attorney, Agent, or Firm*—M. J. Moran

[57] ABSTRACT

A grounding switch device for a metal-clad switchgear is adapted to be inserted into a standard circuit breaker cell allows the bus and line conductors within the switchgear assembly to be grounded for maintenance. A plurality of fixed and selectable test ports are provided to facilitate various electrical tests. The ground switch device is disposed on a frame and contains a ground contact assembly for providing sliding contact between the ground switch device and the ground bus within the circuit breaker cell. The ground contact assembly is in electrical contact with a movable contact. The movable contact is adapted to engage a stationary contact mounted on a mounting plate, attached to the frame by way of an insulator. A selector switch assembly connects the stationary contact to either the upper bus terminals or line terminals in the metal-clad switchgear assembly. The contact portion of the movable contact is U-shaped having two spaced-apart blades. Each blade is adapted to be received in a jaw portion of the stationary contact assembly. The jaw portions of the stationary contact assembly are formed by a pair of U-shaped current loops having inwardly facing protrusions disposed intermediate the bight portion. These protuberances force the contact arm into the jaw when the switch is closed on a live circuit. A combination spring and damper is disposed adjacent the protrusion to provide contact pressure when the ground switch contacts are closed and also to prevent contact bounce which can cause arcing and welding of the assembly.

24 Claims, 3 Drawing Sheets

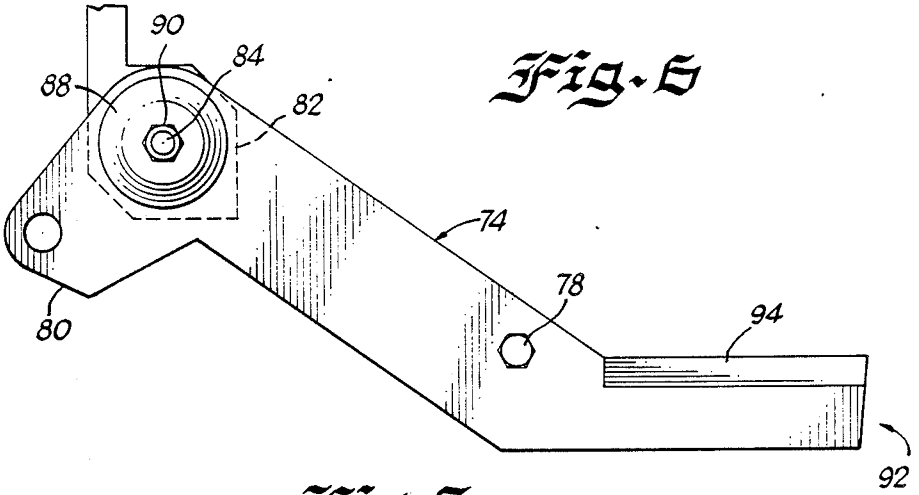
Fig. 6
Fig. 7
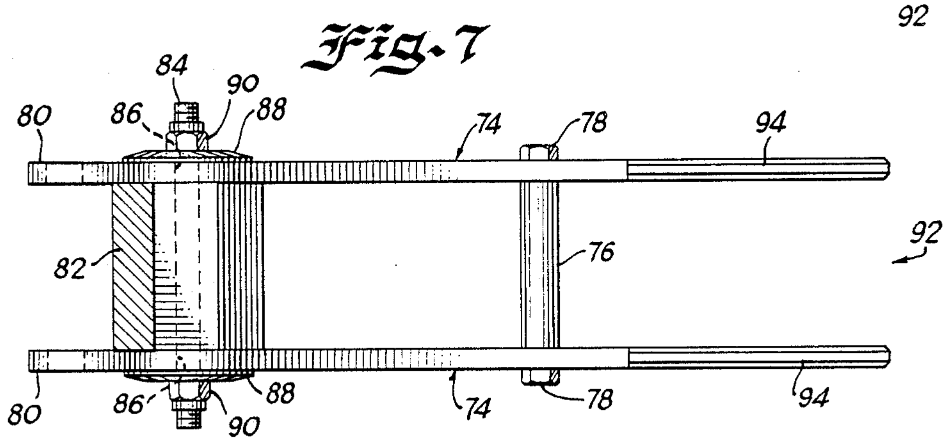
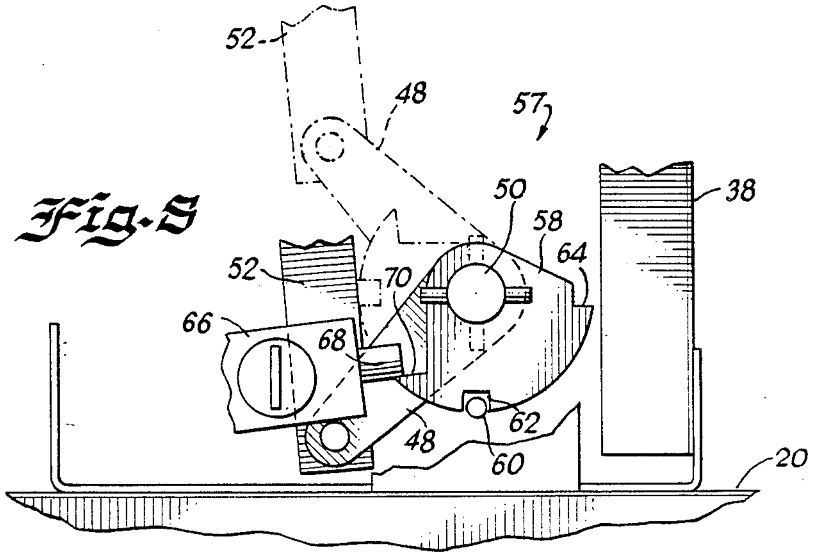
Fig. 8

CONTACT STRUCTURE FOR GROUNDING SWITCH

FIELD OF THE INVENTION

The invention relates to a ground switch device for metal-clad switchgear and more particularly to a contact assembly formed with a plurality of magnetic repulsion loops which assist closing of the contacts when the device is closed on a live circuit. Dampers are also provided in the magnetic repulsion loops to prevent contact bouncing which can cause arcing and welding of the grounding switch contacts.

BACKGROUND OF THE INVENTION

Metal-clad switchgear assemblies are typically used to connect a plurality of electrical loads to a common electrical bus. Such assemblies are typically provided with a plurality of circuit breakers having one side connected to the common bus and the other side connected to various remote electrical loads. The circuit breakers provide electrical protection to isolate the loads during overcurrent conditions, such as an overload or short circuit condition.

The circuit breakers provided in such metal-clad switchgear assemblies are typically drawout devices which may be removed from the switchgear assembly. The circuit breaker assemblies are provided with outwardly extending line and bus contacts which are adapted to automatically engage the line and bus terminals in the metal-clad switchgear assembly when the circuit breaker assembly is inserted into a cell or compartment in the metal-clad switchgear assembly.

Occasionally it is necessary to service the bus structure within the metal-clad switchgear assembly. In such situations, a circuit breaker assembly is removed from the metal-clad switchgear assembly and replaced with a ground switch assembly. The ground switch assembly allows either the line or bus terminals to be grounded during maintenance for personnel safety. Prior to grounding the line or bus terminals within the metal-clad switchgear assembly, it is customary to disconnect the upstream source of electrical power supplying the switchgear assembly. However, under certain conditions, it may be desirable to ground a live circuit. Another situation arises wherein the upstream source of electrical power is inadvertently reenergized during bus maintenance prior to closing of the ground switch. In both such situations, it is necessary to prevent injury to personnel and damage to the equipment.

These dangers can be minimized by insuring that the grounding switch contacts fully close in such a situation. In some known grounding switch devices, contact assemblies are provided which contain current loops which act to increase the contact pressure once the grounding switch is fully closed but may repel the contacts due to the magnetic repulsion forces when the ground switch is being closed in on a live circuit.

It is also important to prevent the contacts from bouncing after the ground switch contacts are closed. Contact bounce results in arcing which may cause the contacts to weld together when the ground switch device is closed in on a live circuit. Once the contacts are welded together, it becomes extremely difficult to remove the grounding switch device from the metal-clad switchgear assembly because of the various mechanical interlocks which prevent the ground switch from being removed when it is in the closed position.

SUMMARY OF THE INVENTION

It is an object of the present invention to solve the problems associated with the prior art ground switch devices.

It is a further object of the present invention to provide a ground switch assembly which includes means for assisting the closing of the contacts when the switch is grounding a live circuit.

It is a further object of the present invention to provide means for reducing contact bounce when the ground switch is closed on a live circuit.

Briefly, the present invention relates to a ground switch for metal-clad switchgear which has a contact configuration which assists in closing the contacts when a live electrical circuit is being grounded. More specifically, the contact assembly is comprised of a stationary contact and a movable contact. A movable contact is formed from a U-shaped member having a pair of spaced-apart, parallel side walls defining blades for engaging the stationary contacts. The stationary contacts are formed with two pairs of spaced-apart, U-shaped current loops. Each pair of current loops forms a jaw for receiving the blades of the movable contacts. Each jaw is provided with inwardly facing protrusions disposed intermediate the leading edge of the bight portion of the U-shaped member to assist in forcing the movable contacts into the jaw when a live circuit is being grounded. Each current loop is provided with a damper which prevents contact bounce to prevent arcing. The dampers also act as a spring when the contacts are closed and provide an additional contact pressure.

DESCRIPTION OF THE DRAWING

These and other objects and advantages will become readily apparent from the following specification in conjunction with the drawing, wherein:

FIG. 6 is a side elevational view of the movable contact in accordance with the present invention;

FIG. 7 is a plan view of the movable contact in accordance with the present invention; and FIG. 8 is a partial front elevational view illustrating the selector switch assembly.

DETAILED DESCRIPTION

Figure 1:
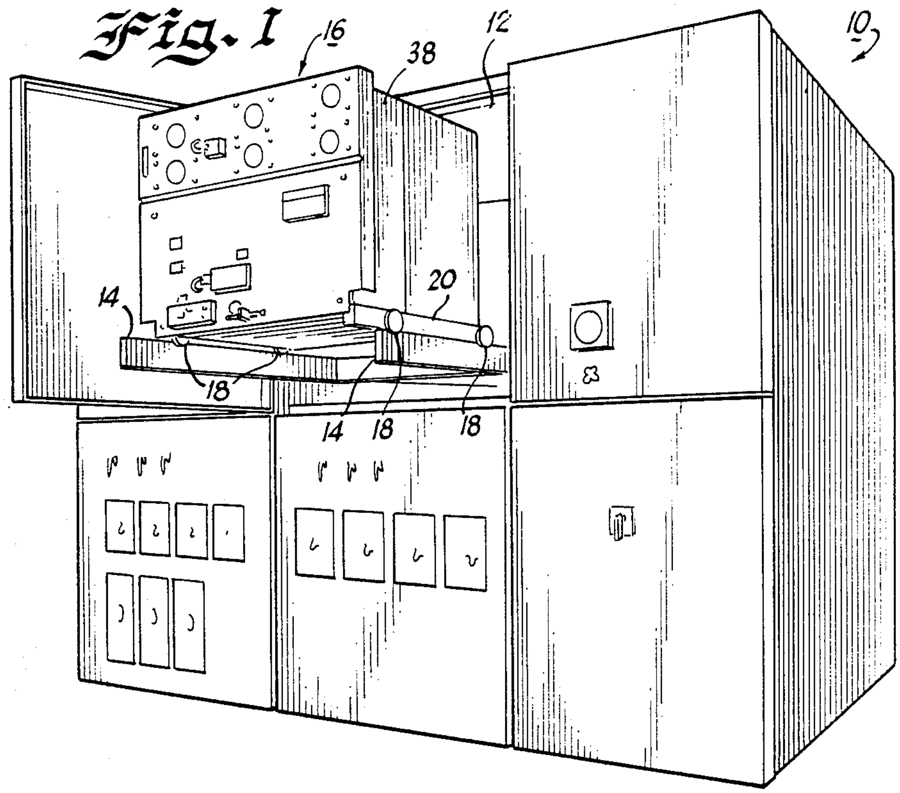
FIG. 1 is a perspective view of a metal-clad switchgear assembly illustrating the ground switch in accordance with the present invention, partially drawn out.

A metal-clad switchgear assembly is generally identified by the reference numeral 10. This assembly 10 contains a plurality of compartments or cells 12. FIG. 1 illustrates six compartments. However, it will be understood that the principles of the invention are applicable to switchgear assemblies having virtually any number of compartments. Each compartment is adapted to receive a draw-out circuit breaker (not shown). The circuit breakers contain a plurality of rollers which are slidingly received on breaker rails 14 to facilitate installation and removal of such circuit breakers. The rear portion of the circuit breakers are provided with extending contacts which are adapted to engage the bus and line terminals in the bus structure when the circuit breaker is fully inserted into a cell 12.

The circuit breakers do not form a part of the present invention. Circuit breakers and metal clad switchgear are generally described in Westinghouse Descriptive Bulletin 32-255, entitled "*VAC Clad - W Medium Voltage Metal Clad Switchgear*" and Bulletin SA-11575, entitled "*World Class Medium Voltage Switchgear With VCP - W Vacuum Circuit Breakers*", which are herein incorporated by reference. The grounding switch device in accordance with the present invention is adapted to be substituted for a circuit breaker such that the line or load bus terminals within the switchgear assembly 10 can be grounded for maintenance.

The grounding device 16 is a draw-out device, similar to the circuit breakers, and contains a plurality of rollers 18 which are rotatably mounted to the chassis 20 of the grounding device assembly 16. The rollers 18 are slidably received on breaker rails 14 to facilitate removal and installation of the grounding switch device assembly 16 into a compartment or cell 12. A ground contact assembly 22 provides a sliding contact interface between the grounding device 16 and the ground bus (not shown) disposed within the cell 12. The ground contact assembly 22 is fixedly attached to the chassis 20. The ground contact assembly 22 is in electrical contact with the movable ground switch contact assembly 24. Thus, once the grounding switch device 16 is inserted into a cell 12, the movable contact assembly 24 is grounded to the cell ground bus.

In a three-pole grounding device 16, three upper contact studs 28 and three lower contact studs are provided. Both the upper contact studs 28 and the lower contact studs 30 are provided with stabs 34 which are used to engage the line and bus terminals in the cells 12. The line and bus terminals in each cell 12 are generally provided with automatic shutters (not shown) to prevent contact with live electrical circuits when the draw out device, either a grounding device assembly 16 or circuit breaker are withdrawn.

The stabs 34 for both the upper contact studs 28 and the lower contact studs 30 are rigidly connected to a rigid conductor 36 and secured to a frame 38. A selector switch bracket 40 is rigidly connected to the rigid conductors 36 and to the frame 38. The selector switch bracket 40 cooperates with a selector switch assembly 26 to connect either the upper contact studs 28 or the lower contact studs 30 to the stationary contact assembly 32.

The selector switch bracket 40 is formed from a relatively flat conductor and bent at one end to form an inclined surface 42. Inwardly facing studs 44 are disposed perpendicular to the inclined surfaces 42 to provide stationary contacts for the selector switch assembly 26.

The selector switch assembly 26 allows either the upper contact studs 28 or the lower contact studs 30 to be connected to the stationary contact assembly 32. Moreover, since a plurality of selectable stud test ports 46 are electrically connected to the stationary contact assembly 32, the selector switch assembly 26 may also be used to connect either the upper contact studs 28 or the lower contact studs 30 to the selectable stud test ports 46.

The selector switch assembly 26 includes an operating lever 48. The operating lever 48 is rotatably mounted about a selector switch shaft 50 at one end. A removable handle (not shown) is received on the selector switch shaft 50 for operating the selector switch assembly 26. The other end of the operating arm 48 is pivotally connected to a lever arm 52. The lever arm 52 is pivotally connected intermediate the ends of a selector switch contact arm 54. One end of the selector switch contact arm 54 is pivotably connected to a mounting plate 56 which forms a portion of the stationary contact assembly 32. The selector switch contact arm 54 is formed from a pair of coextensive arms fastened together. The free end of the selector switch contact arm 54 is formed into a cavity (not shown) for receiving the selector switch contact studs 44 disposed on the selector switch brackets 40 for connecting either the upper contact studs 28 or the lower contact studs 30 to the stationary contact assembly 32.

A selector switch interlock assembly 57 is provided, which includes an interlock plate 58 and a spring loaded latch pin 60. In an at-rest position, the latch pin 60 is captured in one of the slots 62 or 64 formed along the peripheral edge of the interlock plate 58 to latch the selector switch assembly 26 in one of two positions. In order to operate the selector switch assembly 26, it is necessary to pull the latch pin 60 outwardly to enable the selector switch assembly 26 to be rotated. The latch pin 60 is manually held in an outward position until the selector switch 26 is in a fully engaged position. In such a position, the slots 62 or 64 will be disposed adjacent the latch pin 60. The latch pin is then released and captured within the slot to secure the selector switch assembly 26 in a fully engaged position.

A key interlock 66 may also be provided to prevent operation of the selector switch assembly 26 in certain circumstances. The key interlock includes a key operated bolt 68 adapted to engage a stop surface 70 disposed on the interlock plate 58 to prevent operation of the selector switch assembly 26 when the key interlock 66 is locked.

As best shown in FIG. 8, the upper position of the operating lever 48 is used to connect the upper contact studs 28 to the stationary contact assembly 32. The lower position of the operating arm 48 illustrates the position when the lower contact studs 30 are connected to the stationary contact assembly 32.

Figure 2:
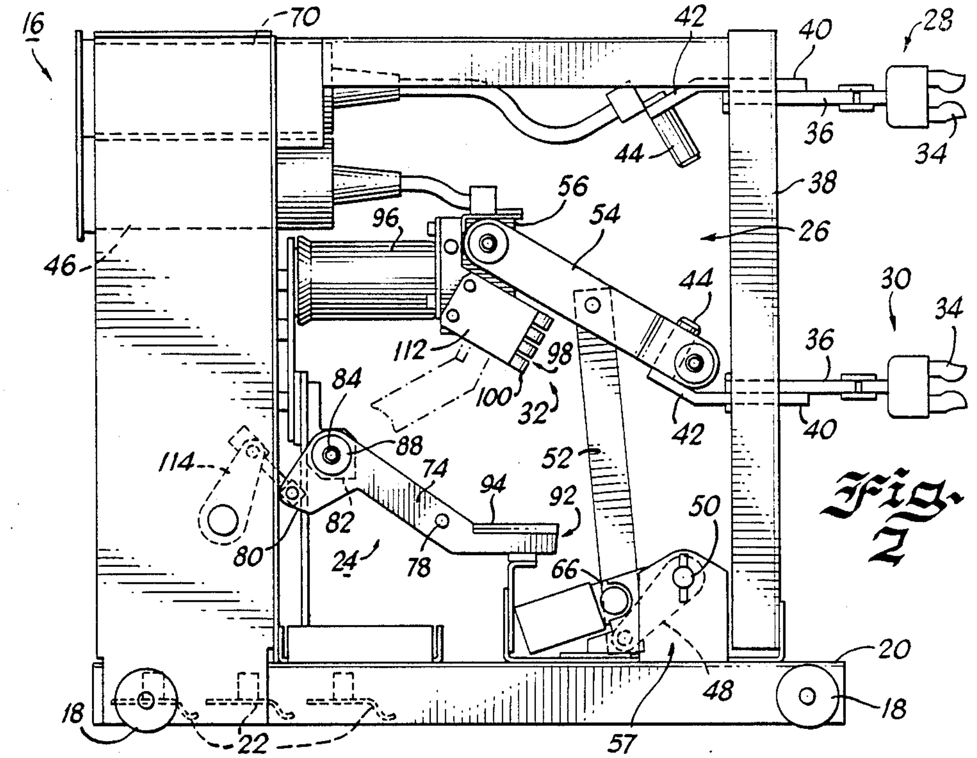
FIG. 2 is a side elevational view of the ground switch in accordance with the present invention shown with the contacts in an open position and the selector switch in a lower position.
Figure 3:
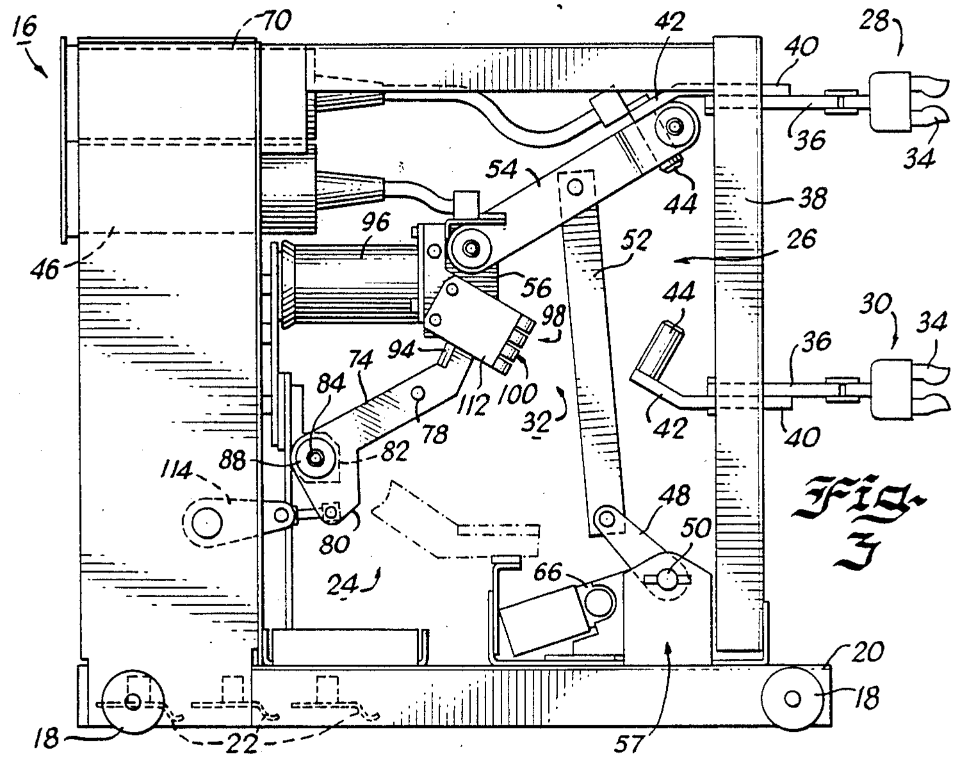
FIG. 3 is a side elevational view of the ground switch device in accordance with the present invention with the ground switch contacts shown closed and the selector switch shown in the upper position.

FIG. 2 illustrates the position of the selector switch assembly 26 in the lower position when the lower contact studs 30 are connected to the stationary contact assembly 32. FIG. 3 illustrates the position of the selector switch assembly 28 when the upper contact studs 28 are connected to the stationary contact assembly 32. Thus, by operating the selector switch assembly 26, the operator can select between the upper contact studs 28 and the lower contact studs 30 to be grounded.

The selector switch assembly 26 also allows the operator to select between having either the upper contact studs 28 or the lower contact studs 30 connected to the selectable stud test ports 46. This allows the ground switch device 16 to be used in cells having different line and bus contact configurations. More particularly, in metal-clad switchgear having upper and lower cells, the configuration of the line and bus terminals may be different between the upper and lower cells. For example, in the stacked cell arrangement, the upper cell may utilize the upper terminals as line terminals and the lower terminals as bus terminals. In a lower cell, the opposite configuration may be true. For example, in a lower cell the top terminals may be used as bus terminals, while the lower terminals are used as line terminals. Thus, the selectable stud test port 46 in conjunction with the selector switch assembly 26 allows either the line or bus terminals in either an upper cell or lower cell to be connected to the selectable stud test port 46.

The selectable stud test port 46 is generally used to determine if the line or bus terminals are dead before closing the ground switch device. Upper stud test ports 72 are also provided. However, these upper stud test ports 72 are generally safety interlocked and are only used in limited circumstances, such as phasing checks. The upper stud test ports 72 are rigidly connected to the selector switch bracket 40 and are thus permanently connected to the upper contact studs 28.

An important aspect of the invention relates to the dynamic ability of the contact assembly to force the movable contact assembly into a fully closed position when the contacts are closed on a live circuit. The stationary contact assembly 32 is also able to prevent contact bounce which can result in arcing which, in turn, can cause the contacts to weld together. Once the contacts have welded together, various mechanical interlocks (which are not a part of the present invention) would prevent the ground switch device 16 from being removed while the switch contacts are closed.

Figure 4:
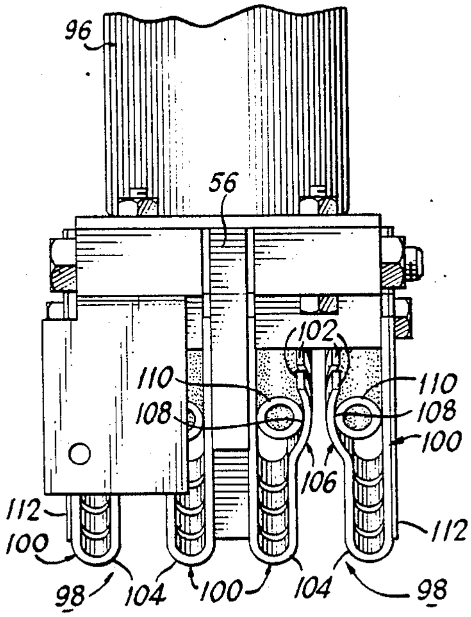
FIG. 4 is a plan view of the stationary contact assembly in accordance with the present invention.
Figure 5:
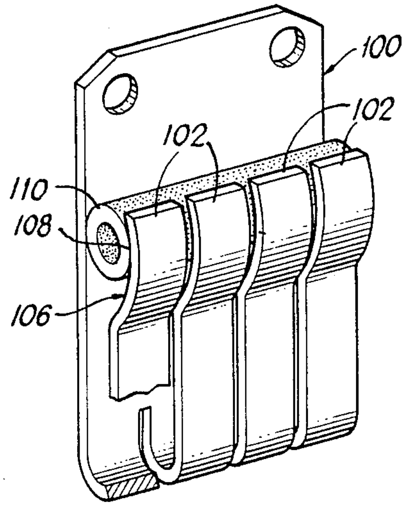
FIG. 5 is a perspective view of one current loop in accordance with the present invention which forms a portion of the stationary contact arm assembly.

FIGS. 4 and 5 illustrate the stationary contact assembly 32 while FIGS. 6 and 7 illustrate the movable contact assembly 24. The movable contact assembly 24 includes a pair of spaced-apart lever arms 74 which are held apart by a spacer 76 having a cylindrical bore therethrough which receives a fastener 78 to secure the lever arms 74 in a spaced-apart relationship. A pivot axis 80 is provided adjacent one end of the assembly 24. The pivot axis 80 is rotatably secured to a mounting plate 82 which is in electrical contact with the cell 12 ground bus.

The pivot axis 80 is formed by providing an axle 84 and a pair of aligned apertures 86 in the lever arm 74. Belleville washers 88 and fasteners 90 are used to secure the axle 84 to the lever arm 74. The free end 92 of the movable contact assembly 24 forms a pair of spaced-apart blades 94 which are received in the stationary contact assembly 32.

The stationary contact assembly 32 is connected to the frame 38 by way of an insulator 96 by way of the mounting plate 56. The stationary contact assembly 32 forms a pair of jaws 98 for receiving the blades 94 of the movable contact assembly 24. Each jaw 98 is formed from a U-shaped member 100. One leg of each U-shaped member is rigidly secured to the mounting plate 56. The free legs of the U-shaped members are provided with protrusions 102 disposed intermediate the bight portion 104 of the U-shaped member 100 defining an arcuate contact portion 106. For each jaw 98, the arcuate contact portions 106 are disposed to be facing each other defining a reduced gap between the U-shaped members 100. Each pair of arcuate contact portions 106 are adapted to receive a blade 94 from the movable contact assembly 24 when the ground switch device 16 is closed.

Disposed adjacent the arcuate contact portions within the cavity 108 formed within the U-shaped members 100 are dampers 110. These dampers 110 are tubular elements and may be formed from sections of pneumatic hose. In order to secure the dampers 110 within the cavity 108, they may be tied to the U-shaped member. The dampers 110 provide spring pressure to reduce contact bounce which can cause arcing and result in the welding together of the contacts. In some conventional devices, once the contacts become welded the mechanical and electrical interlocks within the grounding device prevent the device from being removed from the switchgear assembly 10. The dampers 110 also provide increased contact pressure when the switch is in a closed position.

Also provided are side panels 112 which are used as stiffeners to stiffen the U-shaped members 100 to allow the use of standard copper conductors, thus obviating the need to use spring-tempered copper alloys. The side panels 112 are rigidly secured to one leg of the U-shaped members 100.

The above-described stationary contact assembly utilizes the magnetic repulsion loops or current loops formed by the U-shaped members 100 to assist in fully closing the contacts when the grounding device 16 is closed on a live circuit. In prior art devices, the magnetic repulsion loops have been utilized in a static manner to maintain a movable contact member between two oppositely disposed loop portions by relying on the fact that the legs of the loop will spread apart due to the magnetic effect of the current flowing in different directions in the two legs of the loop. By disposing the arcuate contact portions 106 intermediate the bight portion 104 of the U-shaped member 100, the magnetic repulsion forces actually assist in driving the movable contact assembly 24 into the jaws 98 and thus the magnetic effect is used in a dynamic sense. More particularly, as the blades 94 enter the jaws 98, the blades 94 will first contact the arcuate contact portions 106. When current begins to flow, the magnetic effect of the repulsion forces will force the blades 94 further into the jaws 98.

The placement of the arcuate contact portions along the U-shaped members 100 is an important aspect of the invention. By providing the arcuate contact portions 106 at a location spaced apart from the bight portion 104 of the U-shaped member 100, the magnetic repulsion forces will actually assist in driving the blades 94 into the jaw when the grounding device 16 is closed on a live circuit. However, if the arcuate contact portions 106 were provided near the bight portion 104 or near the tip of the loop the magnetic repulsion forces would force the blades 94 out of the jaws 98. Thus, it should be clear that a unique contact assembly 24 and 32 have been described which utilize the loop effect in a dynamic sense to assist in closing the contacts on a live circuit. Furthermore, the dampers 110 reduce the amount of contact bounce which will, in turn, reduce arcing and minimize the likelihood of welding of the contacts.

The grounding device 16 is also provided with a stored energy device connected to the drive arms 114, used to open and close the contacts. The stored energy device may be electrically closed and mechanically tripped or electrically closed and tripped. The stored energy operator for the grounding device is similar to the stored energy operators utilized in metal-clad switchgear circuit breakers and does not form a part of the present invention. Moreover, grounding devices 16 are provided with numerous mechanical, electrical and key operated interlocks which are generally known and also do not form a part of the present invention.

Thus, it should be apparent that a unique grounding device has been disclosed for use in metal-clad switchgear assemblies. There are many ways in which this device can be implemented, all of which are contemplated to be within the scope of the appended claims.

What is claimed and desired to be secured by Letters Patent of the United States is:

1. A metal-clad switchgear assembly having a circuit breaker cell, bus terminal, line terminal and a ground bus including a ground switch device, wherein said ground switch device, comprises:

a frame;

a stationary and a movable contact connected to said frame and adapted to be electrically connected to said line and bus terminals when said ground switch device is disposed in said cell, wherein said stationary contact includes one or more U-shaped members defining a current loop, wherein said U-shaped members are provided with a protrusion disposed intermediate a bight portion of the U-shaped member; and means for selectively grounding said contacts to said ground bus including means for magnetically assisting the grounding of said contacts when said contacts are connected to live electrical circuits.

2. A metal-clad switchgear assembly having a circuit breaker cell, bus terminal, line terminal and a ground bus including a ground switch device, wherein said ground switch device, comprises:

a frame;

a stationary and a movable contact connected to said frame and adapted to be electrically connected to said line and bus terminal when said ground switch device is disposed in said cell, wherein said stationary contact includes one or more U-shaped members defining a current loop, wherein means are provided for providing additional contact pressure between said stationary contact and said movable contact; and means for selectively grounding said contacts to said ground bus including means for magnetically assisting the grounding of said contacts when said contacts are connected to live electrical circuits.

3. A ground switch device as recited in claim 2, wherein said providing means is disposed adjacent said U-shaped members.

4. A ground switch device as recited in claim 3, wherein said providing means comprises a tubular member.

5. A metal-clad switchgear assembly having a circuit breaker cell, bus terminal, line terminal and a ground bus including a ground switch device, wherein said ground switch device, comprises:

a frame;

a stationary and a movable contact connected to said frame and adapted to be electrically connected to said line and bus terminal when said ground switch device is disposed in said cell, wherein said stationary contact includes two U-shaped members defining a jaw, wherein an end of each U-shaped member is secured to a plate such that the free ends are spaced apart and inwardly face each other defining a jaw with a gap therebetween, wherein the U-shaped members are formed such that the gap adjacent the bight portion of the U-shaped members is relatively larger than the gap intermediate the bight portion; and means for selectively grounding said contacts to said ground bus including means for magnetically assisting the grounding of said contacts when said contacts are connected to live electrical circuits.

6. A ground switch device as recited in claim 5, wherein said U-shaped members are provided with protrusions intermediate the bight portions.

7. A ground switch device as recited in claim 6, wherein said protrusions are integrally formed with said U-shaped member.

8. A ground switch device as recited in claim 6, wherein said protrusions are formed as arcuate contact engaging portions.

9. A metal-clad switchgear assembly having a circuit breaker cell, bus terminal, line terminal and a ground bus including a ground switch device, wherein said ground switch device, comprises:

a frame;

a stationary and a movable contact connected to said frame and adapted to be electrically connected to said line and bus terminal when said ground switch device is disposed in said cell; and means for selectively grounding said first and second contacts to said ground bus including means for magnetically assisting the grounding of said contacts when said contacts are connected to live electrical circuits, further including a damper for reducing arcing caused when said line or bus contacts are connected to a live electrical circuit when said contacts are connected to said ground bus.

10. A ground switch device as recited in claim 9, wherein said damper is disposed adjacent the contacts.

11. Metal-clad switchgear having a circuit breaker cell, bus terminal, line terminal and a ground bus including a ground switch device comprising;

a frame;

a movable contact and a stationary contact, one or the other adapted to be electrically connected to said line and bus terminal and the other contact adapted to be electrically coupled to said ground bus when said ground switch device is disposed in said switchgear; and a damper for preventing contact bounce between said stationary and movable contacts.

12. A ground switch device as recited in claim 11, wherein said damper is disposed adjacent the stationary contact.

13. A ground switch device as recited in claim 12, wherein said damper is a tubular member.

14. Metal-clad switchgear assembly having a circuit breaker cell, bus terminal, line terminal and a ground bus including a ground switch device, wherein said ground switch device, comprises:

a frame;

a stationary and a movable contact connected to said frame and adapted to be electrically connected to said line and bus terminals when said ground switch device is disposed in said cell, wherein said stationary contact includes one or more U-shaped members defining a current loop;

a pneumatic hose disposed adjacent said U-shaped members for providing pressure between the stationary contact and the movable contact; and means for selectively grounding said contacts to said ground bus including means for magnetically assisting the grounding of said contacts when said contacts are connected to live electrical circuits.

15. Metal-clad switchgear assembly having a circuit breaker cell, bus terminal, line terminal and a ground bus including a ground switch device comprising:

a frame;

a movable contact and a stationary contact, one or the other adapted to be electrically connected to said line and bus terminal and the other contact adapted to be electrically coupled to said ground bus when said ground switch device is disposed in said switchgear; and a pneumatic hose disposed adjacent said stationary contact for preventing contact bounce between said stationary and movable contacts.

16. A stationary contact assembly for a ground switch device utilized with metal-clad switchgear comprising:

a pair of U-shaped members defining bight portions, each U-shaped member having one leg connected to a rigid member such that the free legs are inwardly facing each other and spaced apart defining a jaw;

a protrusion disposed on each U-shaped member intermediate the bight portion; and pneumatic hose disposed adjacent the protrusion for increasing the contact pressure of the U-shaped members.

17. A stationary contact assembly for a ground switch device utilized with metal-clad switchgear comprising:

a pair of U-shaped members defining bight portions, each U-shaped member having one leg connected to a rigid member such that the free legs are inwardly facing each other and spaced apart defining a jaw;

a protrusion disposed on each U-shaped member intermediate the bight portion.

18. A stationary contact assembly as recited in claim 17 wherein said protrusion is integrally formed with said U-shaped member.

19. A stationary contact assembly as recited in claim 18, wherein said protrusion is formed as an arcuate surface.

20. A stationary contact assembly as recited in claim 17, further including means for stiffening said leg connected to said rigid member.

21. A stationary contact assembly as recited in claim 17, further including means for increasing the contact pressure of the U-shaped members.

22. A stationary contact assembly as recited in claim 21, wherein said increasing means includes a damper.

23. A stationary contact assembly as recited in claim 22, wherein said damper is disposed adjacent the protrusion.

24. A stationary contact assembly as recited in claim 23, wherein said damper is formed from a tubular element.

* * * * *